United States Patent [19]

Konrad et al.

[11] Patent Number: 5,037,446
[45] Date of Patent: Aug. 6, 1991

[54] 2-NITROANILINE DERIVATIVES AND HAIR DYEING COMPOSITIONS CONTAINING SAME

[75] Inventors: Eugen Konrad, Darmstadt; Thomas Clausen, Alsbach, both of Fed. Rep. of Germany; Hans-Jürgen Braun, Marly; Herbert Mager, Fribourg, both of Switzerland

[73] Assignee: Wella Aktiengesellschaft, Darmstadt, Fed. Rep. of Germany

[21] Appl. No.: 283,311

[22] Filed: Dec. 12, 1988

Related U.S. Application Data

[63] Continuation of Ser. No. 132,789, Dec. 10, 1987, Pat. No. 4,835,414, which is a continuation of Ser. No. 801,615, Nov. 25, 1985, abandoned.

[51] Int. Cl.$^5$ .................................................. A61K 7/13
[52] U.S. Cl. .......................................... 8/414; 8/405; 8/407; 8/408; 8/423
[58] Field of Search .................. 8/405, 414, 408, 407, 8/423

[56] References Cited

U.S. PATENT DOCUMENTS

| | | | |
|---|---|---|---|
| 2,750,326 | 6/1956 | Eckardt et al. | 8/414 |
| 3,591,638 | 7/1971 | Halasz | 564/441 |
| 3,642,423 | 2/1972 | Bil et al. | 8/414 |
| 3,733,175 | 5/1973 | Alperin et al. | 8/409 |
| 4,835,314 | 5/1989 | Konrad et al. | 8/414 |

OTHER PUBLICATIONS

Sagarin, Cosmetics Science and Technology, 1957 pp. 502–507.
Colour Index, 3rd Ed, vol. 4, pp. 4070, 4389, 4537, and 4540.
Feitelson et al., Some Beniminazole Derivatives, 1952 Paper #448, pp. 2389–2398.
Medici et al., Cytotoxic Compounds Part 22, pp. 2517–2520.
Zviak, The Science of Hair Care, Marcel Dekken, Inc. 1986, pp. 247 and 266–267, ISBN 0-8247-7378-0.

Primary Examiner—Paul Lieberman
Assistant Examiner—J. E. Darland
Attorney, Agent, or Firm—Michael J. Striker

[57] ABSTRACT

The composition for dyeing hair yellow contains 2-nitroaniline derivatives of the general formula I:

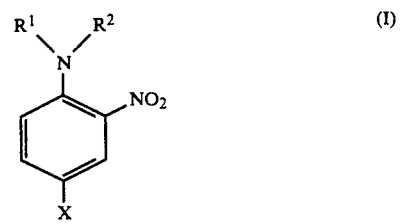

in which, $R^1$ and $R^2$ represent, independent of one another, hydrogen an alkyl of 1 to 4 carbon atoms, a monohydroxyalllkyl of 2 to 4 carbon atoms or a dihydroxyalkyl of 3 or 4 carbon atoms, provided that $R^1$ and $R^2$ do not simultaneously represent alkyl groups of 1 to 4 carbon atoms, and X denotes an alkyl, monohydroxyalkyl, perfluoroalkyl or halogen. Also disclosed are new 2-nitroanitrile derivatives of the general formula II:

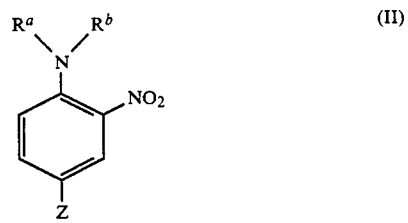

in which $R^a$ and $R^b$ denote, independent of one another, ethyl, a monohydroxylalkyl of 2 to 4 carbon atoms or a dihydroxyalkyl of 3 or 4 carbon atoms, when Z is methyl, Cl or Br; or when Z is $CH_2OH$ or a perfluoroalkyl, $R^a$ denotes hydrogen, a monohydroxyalkyl of 2 to 4 carbon atoms or a dihydroxyalkyl of 3 or 4 carbon atoms, and $R^b$ represents 2-hydroxyethyl or 2,3-dihydroxypropyl.

11 Claims, No Drawings

2-NITROANILINE DERIVATIVES AND HAIR DYEING COMPOSITIONS CONTAINING SAME

This application is a continuation under 37 CFR 1.60 of application Ser. No. 132,789, filed Dec. 10, 1987, now U.S. Pat. No. 4,835,414 which, in turn, is a continuation of application Ser. No. 801,615, filed Nov. 25, 1985.

The present invention relates to the use of certain novel 2-nitroaniline derivatives as nitro dyes in compositions for dyeing hair.

Nowadays, nitro dyes find a wide application in hair dyes. Such dyes are used in oxidation hair compositions as additives for producing natural or fashionable color tones. However, by combining a plurality of differently dyed nitro dyes, it is also possible to produce hair dyeing composition which are able to dye hair in natural to fashionable tones without the use of oxidation compositions.

As an example of blending differently dyed nitro dyes, a natural appearing brown coloration may be generated by the combination of an orange coloring with a blue coloring nitro color. In addition, it is also possible to obtain a similar result with a yellow coloring and a violet coloring nitro color. Therefore, yellow nitro dyes are required which are able to color hair either to an intensive pure lemon yellow, which must be substantially free from red constituents, or into an orange color which can be used with pure blue dyes.

In addition, such nitro dyes must satisfy numerous other requirements. The nitro dyes must be toxicologically and dermatologically acceptable. Their use in oxidation hair dyeing compositions assumes that they are stable in the presence of hydrogen peroxide in alkaline solutions. Moreover, a good light, acid and friction genuiness must be met for the generated hair dyes. Finally, the nitro compositions should be able to be made simply and economically.

The substituted amino-nitrophenols, which have been described in the prior art, satisfy the aforesaid requirements for a yellow coloring of hair only in an insufficient manner. The 4-nitro-3-(2'hydroxyethylamino)-phenol mentioned in the *International Journal of Cosmetic Science*, pp. 25–35 (1982), results in a rather weak lemon yellow color. Two other isomers, namely, the 4-nitro- and the 5-nitro-2-(2'-hydroxyethylamino)-phenol, provide no yellow coloring but, rather, orange coloring nitro dyes which are pH-sensitive, in view of the aromatic hydroxyl groups, and show undesirable color changes during acid and alkali reactions.

Additional yellow nitro dyes known in the art are the o-, m- and p-nitroaniline derivatives mentioned in the DE-AS 1 619 395. These compounds substantially meet the chemical and related application requirements, but are unsatisfactory in view of their physiological characteristics.

It has been surprisingly found that the disadvantages plaguing the prior art can be removed by the use of 2-nitroaniline derivatives of the general formula I:

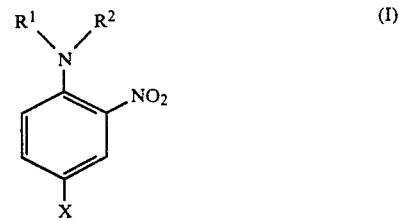

wherein $R^1$ and $R^2$ represent, independently of one another, hydrogen, an alkyl of from 1 to 4 carbon atoms, a monohydroxylalkyl of from 2 to 4 carbon atoms or a dihydroxyalkyl of 3 or 4 carbon atoms, provided that $R^1$ and $R^2$ do not simultaneously represent alkyl radicals of 1 to 4 carbon atoms, and X denotes one radical of the group alkyl, monohydroxyalkyl, perfluoroalkyl or halogen, as a dye in a hair dyeing composition.

By varying the radical X in the compounds of formula I, dye compositions are available to supply all required color tones from a bluish tint lemon yellow to a pure yellow to orange.

Of all the compounds disclosed by formula I, the use of 2-nitroaniline derivatives of the general formula II are preferred for color and physiological reasons

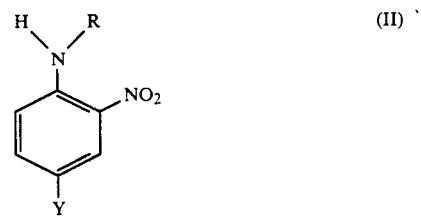

whereby R represents the substituents 2-hydroxethyl or 2,3-dihydroxypropyl, and Y represents $CH_3$, $CF_3$, $CH_2OH$, Cl or Br, as a nitro dye compound in hair dyeing compositions.

Examples of suitable 2-nitroaniline derivatives in accordance with the invention of formula I are 4-amino-3-nitro-toluene, 4-amino-3-nitrobenzyl alcohol, 4-amino-3-nitro-1-trifluoromethyl-benzene, 4-amino-3-nitro-chlorobenzene and 4-amino-3-nitro-bromobenzene, 4[bis-(2'-hydroxyethyl)-amino]-3-nitrotoluene, 4-[N-ethyl,N-(2'-hydroxyethyl)-amino]-3-nitro-toluene, 4-[bis-(2'-amino)-3-nitro-chlorobenzene, 4-[N-ethyl,N-(2'-hydroxyethyl)-amino]-3-nitro-chlorobenzene.

Preferred compounds in accordance with the general formula II are, for example, 4-(2'-hydroxyethyl)-amino-3-nitro-toluene, 4-(2'-hydroxyethyl)-amino-3-nitrobenzyl alcohol, 4-(2'-hydroxyethyl)-amino-3-nitro-1-trifluoro-methylbenzene, 4-(2',3'-dihydroxypropyl-amino-3-nitro-1-trifluoro-methylbenzene, 4-(2'-hydroxyethyl)-amino-3-nitro-chlorobenzene, 4-(2'hydroxyethyl)-amino-3-nitro-bromobenzene and 4-(2',3'-dihydroxypropyl)-amino-3-nitro-bromobenzene.

Surprisingly, the toxicological and physiological characteristics of the compositions in accordance with the general formula I are very good. The dyes with an hydroxylethyl-amino group and with X being methyl, trifluoromethyl, chlorine and bromine in the Ames test are not mutagen and are therefore preferred. These compounds are also preferred for reasons of solubility and color depth, with respect to the nonhydroxylalkylized nitroaniline derivatives.

The novel compositions in accordance with the invention of general formula I represent excellent and quite suitable yellow dyeing nitro dyes for dyeing human hair. Furthermore, the inventive compounds are highly soluble in water and have a good storage capability.

The present invention also provides compositions for dyeing hair with a dye content and common cosmetic additives, characterized in that such compositions contain a 2-nitroaniline derivative of the general formula I. Of these compositions, those containing a 2-nitroaniline derivative of formula II are preferred.

The compositions for dyeing hair in accordance with the present invention may be used without the addition of an oxidation agent or with an oxidation agent, as required.

Hair dyeing compositions which may be used without adding an oxidation agent, and which may contain other dyes outside the scope of the invention, can be applied directly to the hair. Of these dyes which are known for hair dyeing, the following are mentioned by way of example: aromatic nitro dyes, e.g., 2-amino-4-nitrophenol, picramic acid, 1-[2'-hydroxyethyl]-amino]-2-amino-4-nitro benzene, 2-nitro-4-[2'hydroxyethyl)-amino]-aniline, 4-bis[(2'-hydroxyethyl)-amino]-1-methylamino-2-nitro-benzol, 2,5-bis-[(2'-hydroxyethyl)-amino]-nitrobenzene, 2-(2'-hydroxyethyl)-amino-4,6-dinitrophenol and 1-amino-4-(2',3'-dihydroxypropyl)-amino-2-nitro-5-chlorobenzene; triphenylmethane dyes, e.g., Basic Violet 1 (C.I. 42,535); azo dyes, for example, Acid Brown 4 (C.I. 14,805); anthraquinone dyes, e.g., Disperse Blue 23 (C.I. 61,545), Disperse Violet 4 (C.I. 61,105), 1,4,5,8-tetraaminoanthraquinone and 1,4-diamino-anthraquinone, whereby the dyes of these classes may have an acid, nonionogenic or basic character depending on the selection of their substituents. Further dyes which can be applied directly to the hair are described, for example, in the book of J. C. Johnson, *Hair Dyes*, pages 3 91 and 113-139, Noyes Data Corp., Park-Ridge (U.S.A.) (1973) (ISBN: 0-8155-0477-2).

The form or preparation of the hair dyes described herein, on the basis of those dyes which can be directly applied to the hair, may be, for example, a solution, in particular, an aqueous or aqueous-alcoholic solution. Preferred forms of preparations are a cream, a gel or an emulsion, whereby such preparations may be sprayed with a propulsion gas or by means of a pump.

The dyes of general formulae I and II should, preferably, be contained in these dyes without the addition of an oxidation agent in a concentration of about 0.01 to 2.0%, by weight, preferably, from 0.01 to 1.0%, by weight. The total content in the dyes directly applied to the hair is within the limits of about 0.01 to 3.0%, by weight.

The pH-value of these dyes is in the range of 3 to 10.5, in particular, at pH 7.5 to 9.5, whereby the adjustment of the desired alkaline pH-value is performed, particularly, with ammonia, but could also be carried out with organic amines, e.g., monoethanol amine or triethanol amine.

Application of the hair dye compositions is performed in the customary manner by applying the composition to the hair in an amount which is sufficient for the hair coloring, whereby the composition remains in contact with the hair for about 5 to 30 minutes. Subsequently, a rinsing is performed with water and, if need be, with an aqueous solution of a weak organic acid, and the hair is dried. Acetic acid, citric acid and wine vinegar, among others, are examples of acids suitable for use as the weak organic acid.

Naturally, the foregoing hair dye compositions without oxidation agent addition may also contain cosmetic polymerisates, whereby a fastening of the hair is obtained simultaneously with the dyeing. Such agents are customarily called toning fixers or dye fixers.

Of the polymerisates which are known in cosmetics for this are, by way of example, polyvinyl pyrrolidone, polyvinyl acetate, polyvinyl alcohol or polyacryl compounds, e.g., acrylic acid or methacrylic acid polymerisates, basic polymerisates of esters from these two acids, and amino alcohols or the salts thereof or quaternizing products, polyacrylnitrile, polyvinyl lactame, as well as copolymerisates of such compounds as, e.g., polyvinyl pyrrolidone-vinyl acetate.

Also, natural polymers, like chitosan (deacetylized chitin) or chitosan derivatives may be used for the above-mentioned purpose.

The polymerisates are contained in the inventive dyeing compositions in the customary amount of 1-5% by weight. The pH-value of the compositions are in the range of from about 6.0–9.0.

The application of this hair dye with the additional fastening is performed in a known manner by moistening the hair with the fastener, fixing the hair into the desired hairdo and subsequently drying.

Naturally, the aforementioned described hair dyes without any oxidation agent addition may contain further additives which are customary for hair dyeing compositions, for example, caring agents, wetting agents, thickeners, softeners, preserving agents and perfume oils as well as other oxidation hair coloring agents mentioned hereinafter.

The present invention also includes, as previously mentioned, hair dyeing compositions requiring the addition of an oxidation agent. The inventive compositions may also contain known oxidation agents which require an oxidative development, in addition to the dyes in accordance with the stated formula I and, if need be, known dyes which can be directly applied to the hair.

These oxidation dyes are mainly aromatic p-diamines and p-amino phenols, for example, p-toluylene diamine, p-phenylene diamine, p-aminophenol and similar compounds which, for the purpose of shading of the dyes, may be combined with so-called modifiers like, e.g., m-phenylene diamine, resorcin, m-aminophenol and others.

Such oxidation dyes which are known and customary for hair dyeing are described at many points in the literature including E. Sagarin, *Cosmetics*, pages 503 ff., Science and Technology (1957), Interscience Publishers, Inc., New York, as well as in the book of H. Janistyn, *Handbuch der Kosmetika und Reichstoffe*, pages 338 ff. (1973).

With the mixtures obtained from these oxidation dyes and the dyes in accordance with general formula I, one can make very good natural blond and brown tones in fashionable shades.

The dyes in accordance with formulae I and II are contained in dyes with oxidation agent additives in a concentration of about 0.01 to 2.0%, by weight, preferably, 0.01 to 1.0%, by weight. The total content of dyes in these dye compositions is about 0.1 to 5.0% by weight.

Oxidation hair dye compositions are generally alkalinic adjusted, preferably to pH-values of about 8.0 to 11.5, whereby the adjustment is performed, in particular, with ammonia. However, other organic amines may be used, for example, monoethanol amine or triethanol amine. Mainly hydrogen peroxide and the addition compounds of the same are considered as an oxidation agent for developing the hair colorings. The form of preparation of these hair dye compositions may be the same as in the hair dye compositions without oxidation agent addition. Preferably, the form of preparation is a cream or a gel.

Customary additives in creams, emulsions or gels are, for example, solvents, e.g., water, lower aliphatic alcohols, for example, ethanol, propanol, isopropanol, glycerin or glycols, such as, e.g., ethylene glycol and propylene glycol, in addition to glycol ether. Furthermore, wetting agents or emulsifiers from the classes of the anionic, cationic, amphoteric or nonionogenic surface active substances, for example, fatty acid sulfates, fatty alcohol ether sulfates, alkyl sulfonates, alkyl benzene sulfates, alkyl trimethyl ammonium salts, alkyl betaine, oxethylized fatty alcohols, oxethylized nonylphenols, fatty acid alkanol amides, oxethylized fatty acid esters; further thickeners, like higher fatty alcohols, bentonite, starch, polyacrylic acid, cellulose derivatives, like carboxylmethyl cellulose, alginates, Vaseline®, paraffin oil and fatty acids as well as caring agents, e.g., lanoline derivatives, cholesterine, pantothenic acid and betaine, in addition to perfume oils and complex formers. The above-mentioned constituents are used in amounts which are customary for such purposes, for example, the wetting agents and emulsifiers are employed in concentrations of about 0.5 to 30% by weight, while the thickener may be contained in the preparations in an amount of about 0.1 to 25% by weight.

The use of the mentioned preparations, wherein the addition of an oxidation agent is required, is performed in a known manner in that the hair dye compositions are admixed with the oxidation agent before the treatment and an amount of the mixture, which is sufficient for dyeing the hair, is applied to the hair, generally, in the amount of 50 to 150 ml. After a reaction time which is sufficient for the hair dyeing, normally 10–45 minutes, a rinsing is performed with water and, if need be, subsequently with an aqueous solution of a weak organic acid, for example, citric acid or wine vinegar, and subsequently the hair is dried.

With respect to the coloring possibilities, the hair dye compositions in accordance with the present invention provide a wide range of the different color shadings, depending on the type of composition of the color components, extending from natural color tones to highly fashionable, shining shades. The dyes are used either in conjunction with hydrogen peroxide or without an oxidation agent, depending on the composition of the dye.

The 2-nitroaniline derivatives of the formulae I and II are partially known. For example, a process for making the following compositions of formula I is described in the literature;

| Substituents | | | |
|---|---|---|---|
| X | R$^1$ | R$^2$ | Literature |
| CH$_3$ | H | H | L. Gattermann. Ber. Dtsch. Chem. Ges. 18, 1483 (1885) |
| CH$_3$ | H | C$_2$H$_4$OH | S. Matsukawa, J. Pharm. Soc. Japan 63, 370–72 (1943) |
| CF$_3$ | H | H | U.S. Pat. No. 2,056,899 |
| Cl | H | H | F. Beilstein et. al., Liebigs Ann. Chem. 182, 99 (1876) |

-continued

| Substituents | | | |
|---|---|---|---|
| X | R$^1$ | R$^2$ | Literature |
| Cl | H | C$_2$H$_4$OH | B. N. Feitelson et. al., J. Chem. Soc. (London), 2389 (1952) |
| Br | H | C$_2$H$_4$OH | B. N. Feitelson et. al., J. Chem. Soc. (London), 2389 (1952) |
| Br | H | CH$_2$CH(OH)—CH$_2$OH | B. N. Feitelson et. al., J. Chem. Soc. (London), 2389 (1952) |
| Br | H | H | V. Meyer et. al., Ber. Dtsch. Chem. Ges. 5, 632 (1872) |
| Br | H | CH$_3$ | J. J. Blanksma, Rec. Trav. Chim. Pays-Bas 21, 273 (1902) |
| C$_4$H$_9$ | H | H | C. Gelzer, Ber. Dtsch. Chem. Ges. 20, 3253 (1887) |
| CH$_2$OH | H | H | J. Meyer et. al., Ber. Dtsch. Chem. Ges. 33, 250 (1900) |

The present invention also relates to new 2-nitroaniline derivatives of general formula III:

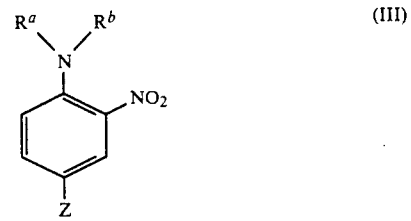

wherein R$^a$ and R$^b$ are independently selected from the group consisting of ethyl, a monohydroxylalkyl having from 2 to 4 carbon atoms and a dihydroxylalkyl having 3 are 4 carbon atoms, when Z is CH$_3$, Cl or Br; or wherein R$^a$ represents hydrogen, a monohydroxyalkyl having from 2 to 4 carbon atoms or a dihydroxyalkyl of 3 or 4 carbon atoms and R$^b$ represents 2-hydroxyethyl or 2,3-dihydroxypropyl, when Z is CH$_2$OH or is perfluoroalkyl. Examples of novel 2-nitroaniline derivatives of formula III are:

4-[bis-(2'hydroxyethyl)-amino]-3-nitrotoluene,
4-[N-ethyl,N-(2'-hydroxyethyl)-amino]-3-nitrotoluene,
4-(2'-hydroxyethyl)-amino-3-nitrobenzyl alcohol,
4-[(2',3'-dihydroxypropyl)-amino]-3-nitro-1-trifluoromethylbenzene.
4-(2'-hydroxyethyl)-amino-3-nitro-1-trifluoromethylbenzene,
4-[bis-(2'-hydroxyethyl)-amino]-3-nitro-chlorobenzene, and
4-[N-ethyl,N-(2'-hydroxyethyl)-amino]-3-nitro-chlorobenzene.

The production of the novel compounds of formula III is performed by nucleophilic exchange of an alkoxy group or a halogen atom (A) in the corresponding Z-substituted composition IV in accordance with the following reaction equation.

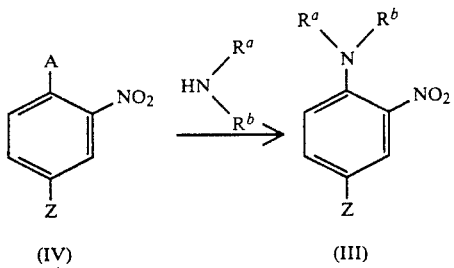

The production of the 2-nitroaniline derivatives of the formulae I, II and III is also possible by nitrification of the protected o-substituted anilines, if need be. Furthermore, the corresponding p-nitroanilines may be brominated or chlorinated for making the 4-chloro- or 4-bromo- derivative of the corresponding o-nitroaniline.

The invention will now be more fully described by the following examples. It should, however, be noted that such examples are given by way of illustration and not of limitation.

MANUFACTURING EXAMPLES

Example 1: Production of 4-[bis-(2'-hydroxylethyl)-amino]-3-nitrotoluene 1.7 g (10 mmoles) 4-chloro-3-nitrotoluene are dissolved in 15 ml diethanolamine and heated for 18 hours to 135° C. Subsequently, this mixture is poured onto ice and extracted with acetic ester. The combined acetic ester phases are dried over sodium sulfate and the solution is evaporated in a vacuum. The desired nitro composition remains as a red oil with impurities of light amounts of side products. A purification is carried out by chromatography on silica gel (operating agent methylene chloride with 5% methanol).

| | CH-Analysis: | |
|---|---|---|
| $C_{11}H_{16}N_2O_4$ | % C | % H |
| calculated: | 54.99 | 6.71 |
| found: | 54.79 | 6.55 |

NMR: 7.50 (s, wide, 2-H), 7.33 and 7.32 (2xs, 5-H, 6-H), 3.65 (t, J=5 Hz, —CH$_2$OH), 3.28 (t, J=5 Hz, —N—CH$_2$—), 2.38 (s, CH$_3$), 2.55-2.25 (wide, OH), 1.57 (wide, H$_2$O).

For the above and the following NMR-spectrums, the following notations apply:
All statements in δ[ppm]
Standard: tetramethylsilane.
Solvent: CDCl$_3$, unless otherwise stated.
s=singulette, d=duplet, t=triplet.
q=quartet, m=multiplet.
UV-spectrum: 251.6 (3.96), 447.5 (2.94).

For the above and all further UV-spectrums, the following notations apply:
Solvent: water.
Statement in λmax [nm] (1 gε).

Example 2: Production of 4-[N-ethyl,N-(2'hydroxyethyl)-amino)]-3-nitrotoluene 1.7 g (10 mmoles) 4-chloro-3-nitrotoluene are heated to 120° C. as in Example 1 for 24 hours in 5.9 ml (5.4 g; 60 mmoles) 2-ethyl-aminoethanol. The preparation as in Example 1 results in a red oil which is purified on silica gel by means of chromatography.

NMR:7.57 (m, 2-H), 7.3-7.2 (m, 5-H, 6-H), 3.62 (t, J=5 Hz, —CH$_2$—OH), 3.28 (t, J=5 Hz, —N—CH$_2$CH$_2$OH), 3.04 (q, J=7 Hz, —N—CH$_2$CH$_3$), 2.35 (s, CH$_3$), 0.98 (t, J=7 Hz, —N—CH$_2$CH$_3$).
UV-spectrum:
250.2 (3.90), 447.4 (2.85).

Example 3: Production of 4-(2'-hydroxyethyl)-amino-3-nitro-benzyl alcohol 1.0 g (5.3 mmoles) 4-chloro-3-nitro-benzyl alcohol are heated with 5 ml ethanol amine to 140° C. After 3 hours the standard is cooled off and is reacted with 15 ml water. The product is extracted 3 times with 40 ml of diethyl ether. The ether phase is washed one time with 20 ml of a saturated common salt solution and is dried over magnesium sulfate. After distilling, the diethyl ether, 0.84 g (4.0 mmoles; 74% of the theoretical yield) of a yellow product remains. The product melts in the range of 89°-90° C.

| | CHN-Analysis: | | |
|---|---|---|---|
| $C_9H_{12}N_2O_4$ | % C | % H | % N |
| Calculated: | 50.94 | 5.70 | 13.20 |
| Found: | 51.17 | 5.78 | 13.11 |

Example 4: Production of 4-[(2',3'-dihydroxypropyl-amino]-3-nitro-1-trifluoromethyl-benzene 23 g (0.10 moles) 4-chloro-3-nitro-1-trifluoromethyl-benzene are heated with 30 g 1-amino-2,3-propandiol for 3 hours to 100° C. After cooling, the product is precipitated with water, vacuumed off and dried. One obtains 26.7 g (93% of the theoretical yield) of a yellow product with a melting range of 117°-118 C.

| | CHN-Analysis: | | |
|---|---|---|---|
| $C_{10}H_{11}F_3N_2O_4$ | % C | % H | % N |
| Calculated: | 42.87 | 3.96 | 10.00 |
| Found: | 42.87 | 3.98 | 9.99 |

Example 5: Production of 4-(2'-hydroxyethyl)-amino-3-nitro-1-trifluoromethyl-benzene 23 g (1.10 moles) 4-chloro-3-nitro-1-trifluoromethyl-benzol are heated to 120° C. with 100 ml ethanol amine for 3 hours. The reaction product is precipitated with water, vacuumed off and dried. After a cooling off, one obtains 23 g (92% of the theoretical yield) of a yellow product with a melting range of 72°-74° C.

| | CHN-Analysis: | | |
|---|---|---|---|
| $C_9H_9F_3N_2O_3$ | % C | % H | % N |
| Calculated: | 43.21 | 3.63 | 11.20 |
| Found: | 43.14 | 3.63 | 11.29 |

Example 6: Production 4-[bis-(2'hydroxyethyl)-amino]-3-nitro-chlorobenzene 4.2 g (22 mmoles) 2,5-dichloro-nitro-benzene are heated for 7 hours in 12.8 ml (14.0 g, 133 mmoles) diethanol amine to 120° C. The reaction mixture is then poured into ice water and is extracted a few times with acetic ester. The combined acetic ester phases are dried over sodium sulfate and the solvent is then evaporated in a vacuum. The obtained orange colored oil may then be purified by chromatography on silica gel (methylene chloride with 2.5% methanol). The pure composition does not crystallize even after a long standing time. Yield: 2.5 g(44% of the theoretical yield)

| | CHN-Analysis: | | |
|---|---|---|---|
| $C_{10}H_{13}N_2O_4Cl$ | % C | % H | % N |
| Calculated: | 46.07 | 5.02 | 10.74 |
| Found: | 46.46 | 5.06 | 10.59 |

Example 7: Production of 4-[N-ethyl,N-(2'-hydroxyethyl)-amino]-3-nitro-chloro-benzene 4.2 g (22 mmoles) 2,5-dichloronitro-benzene are reacted as in Example 6 with 11.8 ml (10.8 g, 120 mmoles) 2-ethyl-amino-ethanol. The preparation, as in Example 6, results in 2.8 g (53% of the theoretical, after purification) of a viscous red oil.

| | CHN-Analysis: | | |
|---|---|---|---|
| $C_{10}H_{13}N_2O_3Cl$ | % C | % H | % N |
| Calculated: | 49.08 | 5.35 | 11.44 |
| Found: | 49.10 | 5.35 | 11.50 |

HAIR DYE EXAMPLES

Example 8: Liquid Hair Dye Composition

| | |
|---|---|
| 0.30 g | 4-(2'-hydroxyethyl)-amino-3-nitrotoluene |
| 2.00 g | lauryl alcohol diglycol ether sulfate-sodium salt (28% aqueous solution) |
| 2.00 g | ammonia, 25% aqueous solution |
| 95.70 g | water |
| 100.00 g | |

Bleached natural hair is treated at room temperature for 20 minutes in accordance with Example 8, subsequently rinsed with water and dried. The hair is dyed yellow orange.

Example 9: Color Fixer

| | |
|---|---|
| 0.10 g | 4-[(2',3'-dihydroxyproply)-amino]-3-nitro-1-trifluoromethyl-benzene |
| 2.00 g | polyvinyl pyrrolidone |
| 0.10 g | glycerin |
| 40.00 g | isopropanol |
| 57.80 g | water |
| 100.00 g | | white human hair is set with the dye fixer solution and dried. The hair is dyed to a shining lemon yellow and is fastened.

Example 10: Oxidation Hair Dye Composition in Cream Form

| | |
|---|---|
| 0.02 g | 4-amino-3-nitro-chlorobenzene |
| 0.20 g | p-phenylene diamine |
| 0.15 g | resorcin |
| 0.03 g | m-aminophenol |

-continued

| | |
|---|---|
| 15.00 g | cetyl alcohol |
| 3.50 g | lauryl alcohol diglycol ether sulfate-sodium salt (28% aqueous solution) |
| 6.00 g | ammonia, 25% |
| 75.10 g | water |
| 100.00 g | |

50 g of the aforementioned hair dye are mixed shortly before use with 50 ml hydrogen peroxide solution (6%). Subsequently, the admixture is applied to gray human hair and is reacted thereon for 30 minutes at a temperature of 40° C. After rinsing of the hair with water and subsequent drying, the hair has assumed a natural blond tone.

Example 11: Hair Dye Composition in Cream Form

| | |
|---|---|
| 0.050 g | 4-(2'-hydroxyethyl)-amino-3-nitro-chlorobenzene |
| 0.250 g | 4-bis-[(2'-hydroxyethyl)-amino-]-1-methylamino-2-nitro-benzene |
| 0.020 g | 1-amino-2-nitro-4-bis-(2'-hydroxyethyl)-amino-benzene |
| 0.025 g | Disperse Blue 23 (C.I. 61,545) |
| 7.500 g | cetyl alcohol |
| 1.750 g | lauryl alcohol-diglycol ether sulfate-sodium salt (28% aqueous solution) |
| 0.100 g | p-hydroxy benzoic acid methyl ester |
| 0.200 g | ammonia, 25% |
| 90.105 g | water |
| 100.000 g | |

50 g of the foregoing hair dye composition were applied to white human hair and rinsed after a reaction time of 20 minutes. Subsequently, the hair is dried to a natural brown color tone.

Example 12: Liquid Hair Dye Composition

| | |
|---|---|
| 0.25 g | 4-(2',3'-dihydroxylpropyl)-amino-3-nitro-bromsbenzene |
| 0.10 g | 1-amino-4-(2',3'-dihydroxyethyl)-amino-2-nitro-5-chlorobenzene |
| 0.20 g | 4-bis-[(2'-hydroxyethyl)-amino]-1-methylamino-2-nitro-benzene |
| 0.50 g | hydroxyethyl cellulose |
| 5.00 g | lauryl alcohol diglycol ether sulfate-sodium salt (28% aqueous solution) |
| 10.00 g | ammonia (25%) |
| 10.00 g | isopropanol |
| 73.95 g | water |
| 100.00 g | |

Bleached natural hair is treated for 20 minutes at room temperature with the solution in accordance with Example 12. After rinsing with water and drying, the hair is a fashionable dark beaujolais tone.

Example 13: Liquid Hair Dye Composition

| | |
|---|---|
| 0.30 g | 4-(2'-hydroxyethyl)-amino-3-nitro-benzyl alcohol |
| 0.05 g | 1,4-bis-(2-hydroxyethyl)-amino-2-nitro-benzene |
| 0.50 g | hydroxyethyl cellulose |
| 5.00 g | lauryl alcohol diglycol ether sulfate-sodium salt (28% aqueous solution) |
| 10.00 g | isopropanol |
| 10.00 g | ammonia, 25% |
| 74.15 g | water |
| 100.00 g | |

The foregoing dye composition is reacted on bleached natural hair for 30 minutes at a temperature of 40° C. After rinsing with water and drying, the hair is dyed in a fashionable blond tone.

While only several embodiments and examples of the present invention have been shown and described, it is obvious that many changes and modifications may be made thereunto, without departing from the spirit and scope of the invention.

What is claimed is:

1. A composition for dyeing hair with a dye content and common cosmetic additives comprising, in an aqueous solution, an aqueous-alcoholic solution, a cream, a gel or an emulsion, 0.01 to 2.0% of a 2-nitroaniline derivative of the formula:

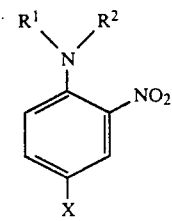

wherein

R$^1$ represents a substituent selected from the group consisting of hydrogen, a monohydroxyl alkyl having from 2 to 4 carbon atoms and a dihydroxyalkyl having 3 to 4 carbon atoms;

R$^2$ represents a substituent selected from the group consisting of monohydroxy alkyl having 2 to 4 carbon atoms and dihydroxy alkyl having from 3 to 4 carbon atoms;

and X represents a substituent selected from the group consisting of an alkyl, monohydroxyalkyl, perfluoralkyl and halogen; and wherein the common cosmetic additives are selected from the group consisting of solvents, including water; lower aliphatic alcohols, including ethanol, propanol, isopropanol and glycerin; glycols, including ethylene glycol and propylene glycol, glycol ethers; wetting agents, emulsifiers including anionic, cationic, amphoteric and nonionogenic surface active substances; fatty alcohols, thickeners, softeners, caring agents, complex formers, perfume oils, other aromatic nitro dyes, triphenylmethane dyes, anthraquinones, ammonia, monoethanol amine, triethanol amine, preserving agents, oxidation hair coloring agents, cosmetic polymerizates and natural polymers and propulsion gas.

2. The composition according to claim 1, wherein said 2-nitroaniline derivative has R$^1$ representing hydrogen, R$^2$ representing a substituent selected from the group consisting of 2-hydroxyethyl and 2,3-dihydroxypropyl, and X representing a substituent selected from the group consisting of CH$_3$, CF$_3$, CH$_2$OH, Cl and Br.

3. The composition according to claim 2, wherein said nitroanilne derivative is 0.01–1.0%, by weight, of said composition.

4. The composition according to claim 3, wherein said 2-nitroaniline derivative is a member selected from the group consisting of 4-(2'-hydroxyethyl)-amino-3-nitrotoluene, 4-(2'-hydroxyethyl)-amino-3-nitrobenzyl alcohol, 4-(2'-hydroxyethyl)-amino-3-nitro-1-trifluoromethyl-benzene, 4-(2',3'-dihydroxypropyl)-amino-3-nitro-1-trifluoromethylbenzene, 4-(2'-hydroxyethyl)-amino-3-nitro-chlorobenzene, 4-(2'-hydroxyethyl)-amino-3-nitro-bromobenzene and 4-(2',3'-dihydropropyl-amino-3-nitro-bromobenzene.

5. The composition according to claim 1, further comprising at least one cosmetic polymerisate contained in an aqueous-alcoholic solution for the purpose of hair fastening.

6. The composition according to claim 5, further comprising at least one other dye in combination with said cosmetic polymerisate.

7. The composition according to claim 6, wherein said other dye is a member selected from the group consisting of 2-amino-4-nitrophenol, picramic acid, 1-[(2'-hydroxyethyl)-amino]-2-amino-4-nitro-benzene, 2-nitro-4-[(2'-hydroxyethyl)-amino]-aniline, 4-bis-[(2'-hydroxyethyl)-amino]-1-methylamino-2-nitro-benzene, 2,5-bis-[(2'-hydroxyethyl)-amino]-nitro-benzene, 2-(2'-hydroxyethyl)-amino-4,6-dinitrophenol, 1-amino-4-(2',3'-dihydroxypropyl)-amino-2-nitro-5-chlorobenzene, Basic Violet 1 (C.I. 42,535), Acid Brown 4 (C.I. 14,805) and Disperse Violet 4 (C.I. 61,105).

8. The composition according to claim 1, further comprising at least one known oxidation hair dye.

9. A process for dyeing hair comprising the step of: applying to hair a composition which includes, in an aqueous solution, cream, gel or emulsion, 0.01 to 2.0% by weight of a 2-nitroaniline derivative of the formula:

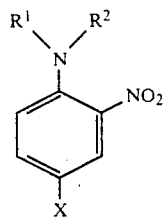

wherein,

R$^1$ represents a substituent selected from the group consisting of hydrogen, a monohydroxyalkyl having from 2 to 4 carbon atoms and a dihydroxyalkyl having 3 to 4 carbon atoms;

R$^2$ represents a substituent selected from the group consisting of monohydroxy alkyl having from 2 to 4 carbon atoms and a dihydroxy alkyl having from 3 to 4 carbon atoms;

and X represents a substituent selected from the group consisting of an alkyl, monohydroxyalkyl, perfluoroalkyl and halogen; and wherein the composition also includes common cosmetic additives selected from the group consisting of solvents, including water; lower aliphatic alcohols, including ethanol, propanol, isopropanol and glycerin; glycols, including ethylene glycol and propylene glycol, glycol ethers; wetting agents, emulsifiers including anionic, cationic, amphoteric and nonionogenic surface active substances; fatty alcohols, thickeners, softeners, caring agents, complex formers, perfume oils, other aromatic nitro dyes, triphenylmethane dyes, anthraquinones, ammonia, monoethanol amine, triethanol amine, preserving agents, oxidation hair coloring agents, cosmetic polymerizates and natural polymers and propulsion gas.

10. The process according to claim 9, wherein said 2-nitroaniline derivative has R$^1$ representing hydrogen, R$^2$ representing a substituent selected from the group consisting of 2-hydroxyethyl and 2,3-dihydropropyl, and X representing a substituent selected from the group consisting of $CH_3$, $CF_3$, $CH_2OH$, Cl and Br.

11. A composition for dyeing hair with a dye content and common cosmetic additives comprising, in an aqueous solution, an aqueous-alcoholic solution, a cream, a gel or an emulsion, 0.01 to 2.0% of a 2-nitroaniline derivative of the formula:

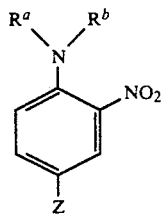

wherein
$R^a$ and $R^b$ are independently selected from the group consisting of ethyl, a monohydroxyl alkyl having from 2 to 4 carbon atoms and a dihydroxyalkyl having 3 to 4 carbon atoms, when Z is selected from the group consisting of $CH_3$ Cl and Br; and wherein $R^a$ represents a substituent selected from the group consisting of hydrogen, a monohydroxyl alkyl having from 2 to 4 carbon atoms and a dihydroxyalkyl having 3 to 4 carbon atoms and $R^b$ represents a substituent selected from the group consisting of 2-hydroxyethyl and 2,3-dihydroxypropyl, when Z is selected from the group consisting of $CH_2CH$ and perfluoroalkyl;

and wherein the common cosmetic additive are selected from the group consisting of solvents, including water; lower aliphatic alcohols, including ethanol, propanol, isopropanol and glycerin; glycols, including ethylene glycol and propylene glycol, glycol ethers; wetting agents, emulsifiers including anionic, cationic, amphoteric and nonionogenic surface active substances; fatty alcohols, thickeners, softeners, caring agents, complex formers, perfume oils, other aromatic nitro dyes, triphenylmethane dyes, anthraquinones, ammonia, monoethanol amine, triethanol amine, preserving agents, oxidation hair coloring agents, cosmetic polymerizates and natural polymers and propulsion gas.

* * * * *